United States Patent
Yokoyama et al.

(10) Patent No.: US 7,223,419 B2
(45) Date of Patent: May 29, 2007

(54) PRODUCTION PROCESS FOR POLYMERIC MICELLE CHARGED THEREIN WITH DRUG AND POLYMERIC MICELLE COMPOSITION

(75) Inventors: Masayuki Yokoyama, Chiba (JP); Eiichi Honzawa, Sodegaura (JP); Yasuaki Ogawa, Kashiwa (JP)

(73) Assignee: Nanocarrier Co., Ltd., Chiba-Ken (JP)

( * ) Notice: Subject to any disclaimer, the term of this patent is extended or adjusted under 35 U.S.C. 154(b) by 421 days.

(21) Appl. No.: 10/666,384

(22) Filed: Sep. 22, 2003

(65) Prior Publication Data
US 2004/0056372 A1    Mar. 25, 2004

Related U.S. Application Data

(63) Continuation of application No. 09/778,901, filed on Feb. 8, 2001, now abandoned.

(30) Foreign Application Priority Data
Feb. 9, 2000    (JP)    ................. 2000-32156

(51) Int. Cl.
*A61K 9/14*    (2006.01)

(52) U.S. Cl. ................. 424/489; 424/489; 424/501; 264/4.1

(58) Field of Classification Search ................ None
See application file for complete search history.

(56) References Cited

FOREIGN PATENT DOCUMENTS

JP    11-335267    *    7/1999

* cited by examiner

Primary Examiner—Michael G. Hartley
Assistant Examiner—James W. Rogers
(74) Attorney, Agent, or Firm—Hahn & Voight PLLC

(57) ABSTRACT

Provided are a production process for a polymeric micelle which is stable and has a high drug content and a composition containing such polymeric micelle. Disclosed are a production process for a polymeric micelle, comprising the steps of dissolving a drug and a specific copolymer in a water non-miscible organic solvent to prepare a solution, mixing the resulting solution with water to form an O/W type emulsion and then slowly volatilizing the organic solvent from the solution, and a polymeric micelle composition charged therein with a water-scarcely soluble drug, which can be obtained by the above production process.

1 Claim, No Drawings

PRODUCTION PROCESS FOR POLYMERIC MICELLE CHARGED THEREIN WITH DRUG AND POLYMERIC MICELLE COMPOSITION

CROSS REFERENCE TO RELATED APPLICATION

This application is a continuation of application Ser. No. 09/778,901, filed on Feb. 08, 2001 now abandoned, which claims foreign priority to JP 2000-32156 filed on Feb. 9, 2000.

TECHNICAL FIELD

The present invention relates to a production process for a polymeric micelle charged therein with a water-scarcely soluble drug and a polymeric micelle composition as a medicinal preparation.

BACKGROUND ART

It is known to use a block copolymer having a hydrophilic segment and a hydrophobic segment for a drug carrier and how to charge a polymeric micelle formed by the above copolymer with a fixed drug (Japanese Patent Application Laid-Open No. 107565/1994 or U.S. Pat. No. 5,449,513). Further, know as well are a composition containing a homogeneous polymeric micelle charged therein with a water-scarcely soluble drug and a preparation method therefor (Japanese Patent Application Laid-Open No. 335267/1999).

Described in Japanese Patent Application Laid-Open No. 107565/1994 is a method in which a micelle is charged therein with a drug by forming in advance a micell of a block copolymer in an aqueous medium, adding a drug to this micelle solution and, if necessary, mixing and stirring it under heating or supersonic treatment. Further, described in Japanese Patent Application Laid-Open No. 335267/1999 is a method for preparing a micelle therein charged with a drug by dissolving a block copolymer and the drug in a water-miscible polar solvent (for example, dimethylformamide, dimethylsulfoxide and acetonitrile) and then dialyzing the solution against water.

According to the conventional techniques described above, it can be found that various advantages are present in use of polymeric micelles as drug carriers. However, there are a case where a content of a drug charged into a polymeric micelle can not be elevated so much depending on the kind of the drug, particularly a water-scarcely soluble drug and a case where a resulting polymeric micelle is not necessarily stable in water or a buffered aqueous solution.

DISCLOSURE OF THE INVENTION

Accordingly, an object of the present invention is to provide a method in which a water-scarcely soluble (or oil-soluble) drug can readily and stably be charged into a polymeric micelle and further to provide a polymeric micelle charged therein with a stable drug which can significantly raise a drug concentration in water or a buffered or isotonic aqueous solution.

The present inventors have found that a drug, particularly a water-scarcely soluble drug can efficiently be charged into a polymeric micelle by simple steps comprising dissolving a drug, particularly a water-scarcely soluble drug and a fixed block copolymer capable of forming a polymeric micelle in an aqueous medium in a water non-miscible organic solvent, preparing an oil-in-water (O/W) type emulsion from the solution thus obtained and water and then volatilizing the organic solvent. Further, they have found as well that suitable selection of the block copolymer used for forming a polymeric micelle makes it possible to homogeneously maintain a water-scarcely soluble drug in a very high concentration in an aqueous medium. The present invention is based on the findings described above.

Thus, according to the present invention, provided as the first embodiment is:

a production process for a polymeric micelle charged is with a water-scarcely soluble drug, comprising the steps of:

(A) dissolving a water-scarcely soluble drug and a block copolymer having a hydrophilic segment and a hydrophobic segment in a water non-miscible organic solvent to prepare an organic solution, (B) mixing the resulting organic solution with an aqueous medium to form an oil-in-water (O/W) type emulsion, (C) vaporizing and removing the above organic solvent from the resulting emulsion to form a polymeric micelle solution charged therein with the above drug, and (D) subjecting the resulting polymeric micelle solution, if necessary, to supersonic treatment and ultrafiltration treatment.

In the production process described above, a wide variety of block copolymers can be used as specifically described later. Among them, block copolymers represented by the following Formula (I) or (II) described in Japanese Patent Application Laid-Open No. 335267/1999 can suitably be used. It is indicated that in the method described in the above gazette, aspartate in which x to y in the following Formula (I) or (II) is 7:3 to 1:3 can not necessarily efficiently be used in charging a water-scarcely soluble drug. It has been confirmed, however, that according to the production process of the present invention, even such block copolymer makes it possible to efficiently charge a polymeric micelle with a drug and that the resulting polymeric micelle charged therein with the drug can stably be present in an aqueous medium.

Accordingly, provided as another embodiment of the present invention is a composition comprising a polymeric micelle originating in a block copolymer charged therein with a drug, wherein the drug is a water-scarcely soluble drug; the block copolymer is represented by the following Formula (I) or (II):

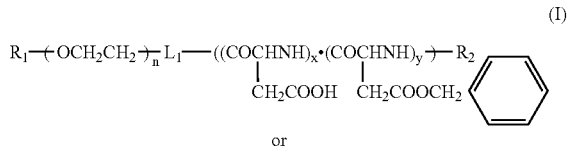

or

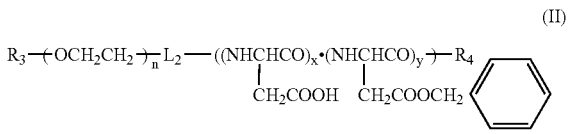

[wherein $R_1$ and $R_3$ each represent a hydrogen atom or a lower alkyl group; $R_2$ represents a hydrogen atom, a saturated or unsaturated $C_1$ to $C_{29}$ aliphatic carbonyl group or an arylcarbonyl group; $R_4$ represents a hydroxyl group, a saturated or unsaturated $C_1$ to $C_{30}$ aliphatic oxy group or an aryl-lower alkyloxy group; $L_1$ represents a linkage group selected from the group consisting of —NH—, —O— and —OCO—Z—NH— (wherein Z represents a $C_1$ to $C_4$ alkylene group); $L_2$ represents a linkage group selected from —OCO—Z—CO— and —NHCO—Z—CO— (wherein Z represents a $C_1$ to $C_4$ alkylene group); n represents an integer of 10 to 2500, preferably 100 to 1000; x and y may be the same or different and represent integers the total of which is 10 to 300, preferably 20 to 100; x to y falls in a range of 3:1 to 0:100, preferably 7:3 to 1:3; x and y each are present at random]; and a micelle solution prepared by dissolving or dispersing the above micelle in water can stably be maintained in a drug concentration of at least 3 mg per ml of the solution.

According to the present invention of this embodiment, a water-scarcely soluble drug which has so far been used in the form of a pharmaceutical preparation for dripping because of difficulty to prepare an aqueous liquid preparation having a high drug concentration can be used in the form of a liquid preparation having a high concentration of an effective ingredient, and it is possible as well to use the water-scarcely soluble drug in the form of an injection preparation which makes it possible to administer a required amount of an effective ingredient for short time.

BEST MODE FOR CARRYING OUT THE INVENTION

The "water-scarcely soluble drug" described in the present invention means such a drug that is not substantially dissolved in an equivalent amount of water under an ambient environment of a room temperature and an atmospheric pressure or is distributed preferentially in a chloroform phase in a solvent system of an equivalent amount of water and chloroform. It shall not be restricted, and capable of being given as such drug are drugs including carcinostatic agents such as adriamycin, paclitaxel, docetaxel, methotrexate, vincristine, topotecan and derivatives thereof, macrolide base antibiotics such as ilotycin, erythromycin and clarislomycin, antifungal agents such amphotericin B, itoraconasol, nystatin and miconasol, steroidal antiinflammatory agents such as dexamethasone and triamcinorone, nonsteroidal antiinflammatory agents such as indometacin and dichlophenac, hormones such as estradiol, testosterone, progesterone, diethylstilbestrol and derivatives thereof, prostaglandin, prostacyclin and other drugs for a central nervous system, drugs for a cardiovascular system and drugs for a digestive system. The method of the present invention is preferably applied to drugs having a solubility of 5 μg/ml or less in water at a room temperature. Among those described above, paclitaxel, docetaxel, camptothecin, topotecan and derivatives thereof can be given as such preferred drugs.

The "block copolymer having a hydrophilic segment and a hydrophobic segment" described in the present invention means a copolymer which can be present in an aqueous medium in the form of a core (mainly comprising hydrophobic segments)-shell (mainly comprising hydrophilic segments) type polymeric micelle and which meets the objects of the present invention. Meeting the objects of the present invention means that a polymeric micelle into which a drug is charged (introduced) can be formed at least by a method described later, and the term that a drug is charged means a state in which the drug is sealed principally in a core part (or area) of a polymeric micelle. The "hydrophilic segment" constituting such block copolymer shall not be restricted and includes segments originating in poly(ethylene oxide), poly(malic acid), poly(saccharide), poly(acrylic acid), poly(vinyl alcohol) and poly(vinylpyrrolidone). On the other hand, the "hydrophobic segment" shall not be restricted and includes segments originating in poly(β-benzyl aspartate), poly(γ-benzyl glutamate), poly(β-alkyl aspartate), poly(lactide), poly(ε-caprolactone), poly(δ-valerolactone), poly(γ-butyrolactone), poly(α-amino acid) and two or more kinds thereof.

Publicly known block copolymers containing such segments can be used as they are or after modified. To be specific, capable of being used as they are or after modified a little are those described in Japanese Patent Application Laid-Open No. 107565/1994 and Japanese Patent Application Laid-Open No. 335267/1999 described above, Japanese Patent Application Laid-Open No. 506961/1995 (=WO 93/16687), WO 96/33233, WO 96/32434 and WO 97/06202. In particular, among the block copolymers described in Japanese Patent Application Laid-Open No. 335267/1999, such block copolymers as specified by Formula (I) or (II) are particularly preferred. According to Japanese Patent Application Laid-Open No. 335267/1999, it is indicated that when a carboxyl group unit

in Formula (I) or (II) described above is an ester with a saturated or unsaturated $C_1$ to $C_{30}$ aliphatic alcohol, particularly an ester with a middle or high alkyl alcohol, it is suited for charging a water-scarcely soluble drug into a polymeric micelle. To be unexpected, however, according to the present invention, in preparing, for example, micelles of paclitaxel, docetaxel, camptothecin and topotecan, the block copolymers having a form represented by Formula (I) or (II) described above in which an aspartate unit is partially hydrolyzed among the block copolymers can more suitably be used in order to stabilize the polymeric micelle charged therein with the drug in an aqueous medium.

Specific examples of the respective groups shown in Formulas (I) and (II) include the following ones. The "short chain alkyl group" represented by $R_1$ and $R_3$ can be a linear or branched chain having 1 to 6 carbon atoms and includes methyl, ethyl, iso-propyl, n-butyl and isoamyl. The "saturated or unsaturated $C_1$ to $C_{29}$ aliphatic carbonyl group or arylcarbonyl group" represented by $R_2$ can be acetyl, propionyl, isopropionyl, decanoyl, dodecanoyl (lauroyl), tetradecanoyl (myristoyl), hexadecanoyl (palmitoyl), octadecanoyl, 9,12-octadecadienoyl (linoloyl), icosanoyl (arachidonoyl) and benzoyl. The "saturated or unsaturated $C_1$ to $C_{30}$ aliphatic oxy group or aryl-lower alkyloxy group" represented by $R_4$ can be methoxy, ethoxy, octyloxy, docosyloxy and benzyloxy.

In general, $L_1$ and $L_2$ are linkage groups which can freely be changed depending on the production process of the block copolymers represented by Formulas (I) and (II). The polymer in which $L_1$ is —NH—, —O— or —OCO—Z—NH— can be obtained when an α-amino acid chain is extended via an amino group shown below by a carbon dioxide-eliminating polymerization method (so-called NCA method) in which after forming a polyoxyethylene segment by anion-living polymerization, a hydroxyl group at a ω-terminal is converted to an amino group or a —OCO—Z—$NH_2$ group (Z is a $C_1$ to $C_4$ alkylene group) and then an N-carboxylic acid anhydride of β-benzyl aspartate is used. Similarly, the polymer in which $L_1$ is —O— includes those obtained by forming a polyoxyethylene segment by anion-living polymerization and extending a polyamino acid segment at a ω-terminal thereof by the NCA method or condensing polyoxyethylene with poly-β-benzyl aspartate which is separately produced by the NCA method.

The block polymer represented by Formula (II) includes usually those which can be provided by separately producing polyoxyethylene and poly-β-benzyl aspartate and then converting a (ω-terminal of polyoxyethylene to a carboxyl group or, if necessary, linking a carboxyl group with an N-terminal amino group of polyamino acid via a $C_1$ to $C_6$ alkylenedicarboxylic acid.

The block copolymer containing a desired extent of the free aspartic acid unit described above can advantageously be produced by subjecting the poly-β-benzyl aspartate segment (or block) described above to a partial hydrolytic reaction. The specific production process of the block copolymer described above is specifically described in Japanese Patent Application Laid-Open No. 335267/1999, and therefore it can be referred to, if necessary.

The present invention shall further be explained below with reference mainly to an example in which the block copolymer represented by Formula (I) is used, and other various block copolymers shall be able to be used as well by modifying a little.

The "water non-miscible organic solvent" described in the present invention means a solvent having a concept opposed to dimethylformamide, dimethylsulfoxide and acetonitrile which are substantially freely miscible with water and which are used for forming a polymeric micelle in Japanese Patent Application Laid-Open No. 335267/1999. It shall not be restricted, and specific examples thereof include chloroform, methylene chloride, toluene, xylene, n-hexane or a mixture thereof.

In a step (A) of the process of the present invention, prepared is a solution obtained by dissolving a drug and a block copolymer in a water non-miscible organic solvent. Such solution can be prepared by separately dissolving the drug and the block copolymer in the solvents and then joining them together or mixing and dissolving the drug and the block copolymer in a single vessel at the same time. If the solution containing a concentrated solute has to be prepared, the solute is dissolved (or homogeneously dispersed) in a large amount of a solvent, and then a fixed amount of the solvent may slowly be distilled off. A preferred range of a mixing ratio of the drug used to the block copolymer can be changed depending on the kind of the drug used and a charging rate of the intended drug and therefore is not specified. In general, it is 1:20 to 2:5, preferably 1:10 to 1:3 in terms of a weight ratio of the drug to the block copolymer.

In a step (B), the organic solution thus prepared is mixed with an aqueous medium to prepare an oil-in-water (O/W) type emulsion. Water (including purified water or ion-exchanged water) or an isotonicity-reduced or buffered aqueous solution containing sodium chloride or a buffer agent can be give as an example of the aqueous medium. However, the aqueous medium may further contain a small amount of a water-miscible organic solvent and other inorganic salts (for example, sodium sulfate and the like) as long as they do not exert an adverse effect to formation of the O/W type emulsion. Usually, the organic solvent and the aqueous medium are mixed in a volume ratio of 1:100, preferably 1:20. Capable of being used for this mixing means are means conventionally used for preparing various emulsions, a mechanical stirrer, a shaker and a supersonic irradiating equipment. An operating temperature of such means shall not be restricted and is set preferably to a range of about −5 to about 40° C. considering a temperature stability of the drug and a boiling point of the solvent.

Thus, the O/W type emulsion is formed, and then the mixing operation described above is continued in an open system or the organic solvent is vaporized and removed (or volatilized and removed) under reduced pressure while stirring. Thus, as volatilization of the organic solvent goes on, the emulsion is changed to a polymeric micelle solution (or dispersion).

The polymeric micelle solution may be subjected to filtering treatment of insolubles and deposited matters by means of a filtering membrane as it is or after subjecting to supersonic treatment if there is a possibility that the polymeric micelle is associated or coagulated. The filtering membrane used shall not be restricted, and a membrane having a pore diameter of about 1 μm is preferred. Further, when the aqueous medium contains sodium chloride, sodium chloride contained in a physiological saline solution is removed by dialysis to obtain a micell medicine. The dialysis membrane shall not be restricted by a material and a pore diameter as long as it can efficiently separate the raw material, solvent, drug and polymer used. Usually, a cellulose membrane is used. After dialysis, supersonic treatment may further be carried out to mono-disperse the associated micelles.

The polymeric micelle according to the present invention is stable in the aqueous medium as described above, and the drug concentration in the liquid preparation can be raised. In order to elevate the drug concentration in this micelle solution (liquid preparation), concentration by filtration or freeze-drying can be carried out.

The method described above makes it possible to control the drug concentration to 10 to 30% by weight based on the total weight of the drug and the copolymer. Further, when the copolymer represented by Formula (I) is used, capable of being provided is the composition of the aqueous medium in which the polymeric micelle can stably be maintained in a drug concentration of about 3 mg, preferably about 6 mg and particularly preferably about 10 mg per ml of the polymer micelle solution. Being capable of stably maintaining the polymeric micelle means that when the above composition is left standing at a room temperature, association between the polymeric micelles and discharge of the drug from the polymeric micelle are not brought about at least for several hours. The above association and discharge of the drug can be confirmed by optical inspection or visual observation.

The present invention shall further be explained below with reference to specific examples, but the present shall not be restricted by these examples.

EXAMPLES 1 TO 4

Effect of a Change in a Proportion of the Drug to the Copolymer

Used was polyethylene glycol (molecular weight: 12000)-co-50% partially hydrolyzed polybenzyl aspartate (n=50) (hereinafter referred to as 12-50PH) (corresponding to the copolymer represented by Formula (I)). Dissolved in 5 ml of chloroform respectively were 50 mg of 12-50PH and 5, 10, 15 and 20 mg of paclitaxel (obtained from Signum Ltd.), and chloroform was distilled off to adjust the amount of the chloroform solution to 0.5 ml after concentration, whereby four kinds of the chloroform solutions having different ratios (in terms of a weight ratio) of the polymer to the drug were obtained (the ratios were 100:10, 100:20, 100:30 and 100:40). They were dispersed in 5 ml of a 5% saline aqueous solution respectively and stirred vigorously for about 30 minutes to obtain four kinds of O/W emulsions. Then, chloroform was distilled off while stirring slowly at a room temperature to obtain polymeric micelle solutions containing paclitaxel. They were filtered by means of a membrane having a pore diameter of 0.45 μm to remove foreign matters, and the drug contents in this stage were determined by means of HPLC. The results thereof are shown in the following Table I.

TABLE I

| | Example number | | | |
|---|---|---|---|---|
| | 1 | 2 | 3 | 4 |
| Drug concentration (%) in charged polymer | 10 | 20 | 30 | 40 |
| Entrapment (%) | 69 | 96 | 71 | 59 |

As apparent from the results shown in Table I, it is shown that the entrapment is high when the polymer and the drug were charged in a ratio of 100:10 to 100:30.

EXAMPLES 5 TO 6

Difference in the Characteristics of the Polymeric Micelles According to the Kind of the Copolymer Used were two components of 12-50PH and polyethylene glycol (molecular weight: 12000)-co-polybenzyl aspartate (n=25) (hereinafter referred to as 12-25).

Used were 50 mg of the respective copolymers and 10 mg of paclitaxel to charge the polymer with the drug in a ratio of 100:20 to prepare polymeric micelles by the same method as in Example 1 (provided that supersonic irradiation was carried out for 15 minutes by means of a probe type supersonic apparatus before filtering by means of a membrane having a pore diameter of 0.45 μm). The drug-charging rates in this stage were 94% in 12-50Ph and 64% in 12-25. The concentrations of the drugs contained in the aqueous solutions in this stage were 1.60 mg/ml and 1.23 mg/ml respectively, and they were further filtered and concentrated. This concentration was carried out by pressurized filtration using Mole Cut L manufactured by Millipore Co., Ltd. Even if concentrated up to 10.9 mg/ml in 12-50PH, nothing abnormal was found in the aqueous solution, and it was possible to further concentrate. In 12-25, however, the solution could be concentrated only to 4.1 mg/ml, and precipitants were adhered to the filtering membrane. As apparent from this result, the more concentrated paclitaxel micelle solution can be prepared in a system using partially hydrolyzed polybenzyl aspartate.

EXAMPLE 7

Precisely weighed into a glass-made centrifugally settling tube was 50 mg of polyethylene glycol-co-50% partially hydrolyzed polybenzyl aspartate (12-50PH), and added thereto was 5 ml of a chloroform solution of paclitaxel having a concentration controlled to 2 mg/ml. It was stirred and dissolved, and then chloroform was distilled off under nitrogen flow to adjust an amount of the chloroform solution to 0.5 ml after concentration. Added thereto was 5 ml of a 5% sodium chloride aqueous solution, and the tube was tightly sealed and vigorously stirred to form an O/W emulsion. The tightly sealed stopper was removed 30 minutes later, and chloroform was distilled off while slowly stirring at a room temperature for a whole day and night, whereby a polymeric micelle aqueous solution charged therein with the drug was obtained. The polymeric micelle solution was irradiated with a probe type supersonic apparatus for 15 minutes by applying intermittent oscillation by every second to sufficiently disperse the micelles. Then, the solution was filtered by means of a filter having a pore diameter of 0.45 μm and further dialyzed to remove sodium chloride. Thereafter, a sodium chloride solution was added to reduce the solution to isotonicity. Further, the solution was pressure-filtered and concentrated by means of an Amicon ultrafilter (UK200 membrane). This provided a polymeric micelle aqueous solution having a paclitaxel concentration of 13.5 mg/ml. This solution had a chloroform content of 5 ppm or less.

EXAMPLE 8

Precisely weighed into a glass-made centrifugally settling tube was 50 mg of polyethylene glycol-co-polybenzyl aspartate (12-25), and added thereto was 5 ml of a chloroform solution of paclitaxel having a concentration controlled to 2 mg/ml. Hereinafter, a polymeric micelle aqueous solution containing paclitaxel was obtained in the same manner as in Example 7. The drug concentration thereof was 3.5 mg/ml.

EXAMPLE 9

Precisely weighed into a glass-made centrifugally settling tube was 50 mg of polyethylene glycol-co-50% partially hydrolyzed polybenzyl aspartate (12-50PH), and added thereto was 5 ml of a chloroform solution of paclitaxel having a concentration controlled to 3 mg/ml. Hereinafter, a polymeric micelle aqueous solution containing paclitaxel was obtained in the same manner as in Example 7. The drug concentration thereof was 6.7 mg/ml.

EXAMPLES 10 TO 13

Used in a glass-made centrifugally settling tube respectively were four kinds of 35, 50, 65 and 75% partially hydrolyzed polybenzyl aspartates (n=50) (12-50PH) of the copolymer. Each 50 mg of the respective polymers was precisely weighed, and added thereto was 5 ml of a chloroform solution of paclitaxel having a concentration controlled to 2 mg/ml to prepare four kinds of solutions. Each was stirred and dissolved, and then chloroform was distilled off under nitrogen flow to adjust an amount of the chloroform solution to 0.5 ml after concentration. Added thereto was 5 ml of a 5% sodium chloride aqueous solution, and the tube was tightly sealed and vigorously stirred to form an O/W emulsion. The tightly sealed stopper was removed 30 minutes later, and chloroform was distilled off while slowly stirring at a room temperature for a whole day and night, whereby four kinds of polymeric micelle aqueous solutions charged therein with the drug were prepared. The polymeric micelle solutions were irradiated with a probe type supersonic apparatus for 15 minutes by applying intermittent oscillation by every second to sufficiently disperse the micelles. Then, the solutions were filtered by means of a filter having a pore diameter of 0.45 μm. The paclitaxel concentrations in a stage before concentration were 1.8, 1.9, 1.6 and 1.7 mg/ml respectively.

EXAMPLE 14

Precisely weighed into a glass-made centrifugally settling tube was 50 mg of polyethylene glycol (molecular weight: 5000)-co-polybenzyl aspartate (n=12) (5-12), and added thereto was 5 ml of a chloroform solution of paclitaxel having a concentration controlled to 2 mg/ml. Each was stirred and dissolved, and then chloroform was distilled off under nitrogen flow to adjust an amount of the chloroform solution to 0.5 ml after concentration. Added thereto was 5 ml of a 5% sodium chloride aqueous solution, and the tube was tightly sealed and vigorously stirred to form an O/W emulsion. The tightly sealed stopper was removed 30 minutes later, and chloroform was distilled off while slowly stirring at a room temperature for a whole day and night, whereby a polymeric micelle aqueous solution charged therein with the drug was prepared. The polymeric micelle solution was irradiated with a probe type supersonic apparatus for 15 minutes by applying intermittent oscillation by every second to sufficiently disperse the micelles. Then, the solution was filtered by means of a filter having a pore diameter of 0.45 μm. Thereafter, a sodium chloride solution was added to reduce the solution to isotonicity. The paclitaxel concentration in a stage before concentration was 1.6 mg/ml.

EXAMPLE 15

Precisely weighed into a glass-made centrifugally settling tube was 50 mg of polyethylene glycol-co-polybenzyl aspartate (12-25), and added thereto was 5 ml of a chloroform solution of paclitaxel having a concentration controlled to 2 mg/ml. It was stirred and dissolved, and then chloroform was distilled off under nitrogen flow to adjust an amount of the chloroform solution to 0.5 ml after concentration. Added thereto was 5 ml of a 5% sodium chloride aqueous solution, and the tube was tightly sealed and vigorously stirred to form an O/W emulsion. The tightly sealed stopper was removed 30 minutes later, and chloroform was distilled off while slowly stirring at a room temperature for a whole day and night, whereby a polymeric micelle aqueous solution charged therein with the drug was prepared. The polymeric micelle solution was irradiated with a probe type supersonic apparatus for 15 minutes by applying intermittent oscillation by every second to sufficiently disperse the micelles. Then, the solution was filtered by means of a filter having a pore diameter of 0.45 μm. The paclitaxel concentration in a stage before concentration was 1.1 mg/ml.

The invention claimed is:

1. A process for the production of a polymeric micelle charged therein with a water-scarcely soluble drug, comprising the steps of:

(A) dissolving a water-scarcely soluble drug and a block copolymer having a hydrophilic segment and a hydrophobic segment in a water non-miscible organic solvent to prepare an organic solution, wherein the block copolymer is represented by the following Formula (I) or (II)

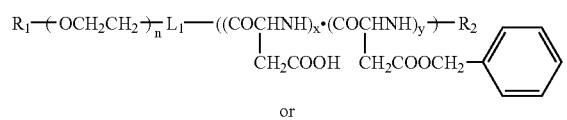

or

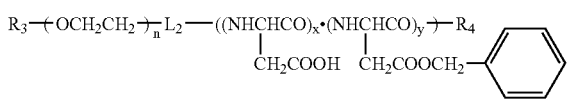

wherein $R_1$ and $R_3$ represent a hydrogen atom or a lower alkyl group; $R_2$ represents a hydrogen atom, a saturated or unsaturated $C_1$ to $C_{29}$ aliphatic carbonyl group or an arylcarbonyl group; $R_4$ represents a hydroxyl group, a saturated or unsaturated $C_1$ to $C_{30}$ aliphatic oxy group or an aryl-lower alkyloxy group; $L_1$ represents a linkage group selected from the group consisting of —NH—, —O— and —OCO—Z—NH— (wherein Z represents a $C_1$ to $C_4$ alkylene group); $L_2$ represents a linkage group selected from —OCO—Z—CO— and —NHCO—Z—CO— (wherein Z represents a $C_1$ to $C_4$ alkylene group); n represents an integer of 10 to 2500; x and y may be the same or different and represent integers the total of which is 10 to 300; x to y falls in a range of 7:3 to 1:3, (B) mixing the resulting organic solution with an aqueous medium to form an oil-in-water (O/W) type emulsion, (C) vaporizing and removing the above organic solvent from the resulting emulsion to form a polymeric micelle solution charged therein with die above drug, and (D) subjecting the resulting polymeric micelle solution, if necessary, to supersonic treatment and ultrafiltraton treatment.

* * * * *

UNITED STATES PATENT AND TRADEMARK OFFICE
CERTIFICATE OF CORRECTION

PATENT NO.       : 7,223,419 B2                                                Page 1 of 1
APPLICATION NO.  : 10/666384
DATED            : May 29, 2007
INVENTOR(S)      : Yokoyama et al.

It is certified that error appears in the above-identified patent and that said Letters Patent is hereby corrected as shown below:

Claims of patent, col. 10, line 44, replace "die" with --the--.

Signed and Sealed this

Seventeenth Day of July, 2007

JON W. DUDAS
*Director of the United States Patent and Trademark Office*